US00PP14267P39

(12) United States Plant Patent
Fleming et al.

(10) Patent No.: US PP14,267 P3
(45) Date of Patent: Nov. 4, 2003

(54) CRAPE MYRTLE PLANT NAMED 'VIOLET FILLI'

(50) Latin Name: *Lagerstroemia indica*
Varietal Denomination: Violet Filli

(76) Inventors: David W. Fleming, Fleming's Flower Fields Inc. 8101 S. 14th St., Lincoln, NE (US) 68512; Gretchen A. Zwetzig, Fleming's Flower Fields Inc. 8101 S. 14th St., Lincoln, NE (US) 68512

( * ) Notice: Subject to any disclaimer, the term of this patent is extended or adjusted under 35 U.S.C. 154(b) by 0 days.

(21) Appl. No.: 09/950,234

(22) Filed: Sep. 10, 2001

(65) Prior Publication Data

US 2003/0051280 P1 Mar. 13, 2003

(51) Int. Cl.[7] ..... A01H 5/00

(52) U.S. Cl. ..... Plt./252

(58) Field of Search ..... Plt./252

*Primary Examiner*—Kent Bell

(57) ABSTRACT

A new and distinct cultivar of dwarf winter hardy Lagerstroemia plant named, 'Violet Filli' is the result of a unique hybridization. This new and distinct cultivar is characterized primarily as to novelty by its extreme cold hardiness to Zone 4, its numerous sturdy bright violet blooms, its compact spreading performance with heavy branching, its vigorous and uniform growth habit, and its floriferous nature form midsummer until frost.

1 Drawing Sheet

Genus/species: *Lagerstroemia indica.*
Varietal denomination: 'Violet Filli'.

BACKGROUND OF THE NEW PLANT

The new plant of this invention is the result of a unique hybridization, with the breeding achievement being evidenced in the outstanding combination of characteristics exhibited by this new and distinct Crape Myrtle ('Violet Filli' *Lagerstroemia indica*) plant, which include:

(a) The plant being very refined and floriferous with flowers that are outstanding for their wide bright violet blooms that compliment the landscape;

(b) The plant being dwarf, but vigorous, with compact and uniformly spiraling spreading action which gives it unique landscape utility;

(c) The plant being very floriferous with flowers that stay open at least 2 full days;

(d) The plant being so hardy that it can consistently withstand winter temperatures of at least −30 degrees Fahrenheit.

SUMMARY OF THE INVENTION

'Violet Filli' was the result of a 40-year breeding program. Its ancestry includes various seedlings of *Lagerstroemia indica.* More specifically, the plant resulted as a selected hardier seedling from the Fleming Crape Myrtle "Filligree" series. 'Violet Filli' resulted from a cross between two unnamed/unpatented Fleming *L. indica* plants.

This new plant first bloomed in the summer of 1978 and was selected by David Fleming and Gretchen Zwetzig on David Fleming's property in Lincoln, Nebr. The plant was observed here under typical conditions for NE, at approximately 3 years of age. Asexual propagation of the plant by cuttings and root division in Lincoln, Nebr., has shown that the unique and distinguishing features of the plant are faithfully transmitted from generation to generation and appear to be fixed. 'Violet Filli' reproduces true to type in successive generations of asexual reproduction.

Since its origin, the plant has bloomed from midsummer until frost, while exhibiting the above-mentioned distinctive characteristics. This hardy crape myrtle plant contributes to the market with its sheer beauty, its compact Growth habit, its great resistance to disease and insects, its stability through extremes in rain and drought, and its Extreme hardiness.

BRIEF DESCRIPTION OF THE DRAWINGS

The flower, bud, foliage, and growth habit of the plant are shown in the attached illustrations. More specifically, Sheet 1 shows a close-up of the blooms and foliage. The colors are as true as is reasonably possible to attain in photographic illustrations of this type. The colors illustrated may be slightly off due to light reflectance.

DESCRIPTION OF THE NEW PLANT

What follows is a detailed description of the new cultivar. The specific color designations set forth by PLATE and number designations are in accordance with the *Dictionary of Color* (*Mearz and Paul*), while general color recitations are consistent with ordinary American color terminology.

'Violet Filli' has not been observed under all possible environmental conditions. It is to be understood that the phenotype may vary significantly with variations in environment such as temperature, light intensity, and day length, without, however any difference in genotype of the plant. The following botanical characteristics and observations are taken from a 3 year old plant when grown under normal outdoors conditions in Lincoln, Nebr.

THE PLANT

The new Crape Myrtle plant differs from the seed parent and pollen parent in the following ways:

TABLE 1

| | 'Violet Filli' | Unnamed Fleming *L. indica* | Unnamed Fleming *L. indica* |
|---|---|---|---|
| Width: | 1 ½ ft. | 3 ft. | 3 ½ ft. |
| Height: | 1 ½ ft. | 3 ft. | 2 ft. |
| Form: | flat globe | upright | globe |
| Hardiness: | −30 degrees Fahrenheit | −25 degrees Fahrenheit | −25 degrees Fahrenheit |
| Branching: | Compact, thick | Medium length | Medium length |
| No. of flowers per day per season: | 35 | 20 | 30 |

*Tree performance.*—From spreading to flat spreading.
*Tree form.*—Flat globe.
*Tree height.*—Dwarf, about 1½ feet.
*Tree width.*—1½ ft.
*Type of trunk.*—Single trunk with approximately 20 to 50 spreading branches.
*Trunk color.*—Brown. 8-C, page 37, PLATE 7.
*Young bud color.*—Cherry red.

Branches:
*Color.*—Brown. 2-C, page 37, PLATE 7.
*Thickness.*—3 cm.
*Average length.*—6–10 inches.
*Branching habit.*—Heavy; 20 to 50 branches in average on main trunk.
*Internode length.*—About ½ inch, 1½ cm.

Foliage:
*Leaves* (*lamina*).—Compact, elliptical with rounded apex and base.
*Margin.*—Entire.
*Average leaf length.*—About 1½ inches, 3¼ cm.
*Average leaf width.*—About ¾ inch, 2 cm.
*Color immature.*—Slightly darker than 1-J, page 69, PLATE 23.
*Upper surface of mature leaf.*—Same as immature leaf color.
*Underside of mature leaf.*—5-B, page 67, PLATE 22.
*Color change.*—Purplish.
*Luster.*—Dull sheen.
*Petiole.*—Green. 5-B, page 67, PLATE 22.
*Length.*—1 cm.

Flower:
*Pedicel length.*—0.5 cm.
*Pedicel color.*—6-G, page 65, PLATE 21.
*Bud shape.*—Rotund to trapezoidal.
*Bud length.*—½ inch.
*Bud width.*—½ inch.
*Bud color.*—5-H, page 35, PLATE 6.
*Cluster.*—Conic, broad.
*Inflorescence.*—11 flowers on average per one cluster.
*Type.*—Cluster.
*Bloom diameter.*—1¾ inches, 4½ cm.
*Number of flowers.*—50 on average per inflorescence.
*Shape or form.*—Single, six petals.
*Fragrance.*—Slight.

Petals:
*Color* (*for both surfaces*).—6-H, pg. 107, PLATE 42.
*Shape.*—Orbiculate with a strong wave.
*Petal length.*—1 inch.
*Petal apex.*—Rounded.
*Petal width.*—¾ inch, 1½ cm.
*Petal margin.*—Smooth or entire.
*Persistence of individual bloom.*—2 days.
*Base.*—Connate.

Reproductive organs:
*Style.*—Pale violet.
*Pistil.*—One.
*Filaments.*—Pale violet.
*Anthers.*—Yellow.
*Stamens.*—30 to 35 arranged around the pistil.
*Pollen.*—Scarce.
*Pollen color.*—1-L, page 43, PLATE 10.

Fruit:
*Shape.*—Rotund; apex ½ cm in width.
*Color.*—Green when immature, matures to purple.

Seeds:
*Color.*—Grayish-brown.
*Size.*—¼ cm.

Growth:
*Habit.*—Dwarf, about 1½ feet.
*Blooming period.*—July until October.

Hardiness: Hardy to at least −30 degrees Fahrenheit, or Zone 4.

General health: Plant is very disease resistant; very pest resistant; sturdy through excessive drought or water.

Time it takes to produce "finished" plant: 2 years for apx. 5 gallon plant.

GENERAL OBSERVATIONS

This plant, as a hybridized hardy Lagerstroemia, is valuable to the landscape market for its improvements in different colored, outstanding flowers, refined foliage, dwarf, compact and uniform breaking action, all-around vigor, and adaptation to extreme environments, including the ability to consistently survive winter temperatures of at least −30 degrees Fahrenheit.

We claim:

1. A new and distinct cultivar of Lagerstroemia plant, as herein shown and described, characterized by its beautiful violet flowers and refined foliage, its dwarf and compact spreading action, its vigor, and its extreme hardiness.

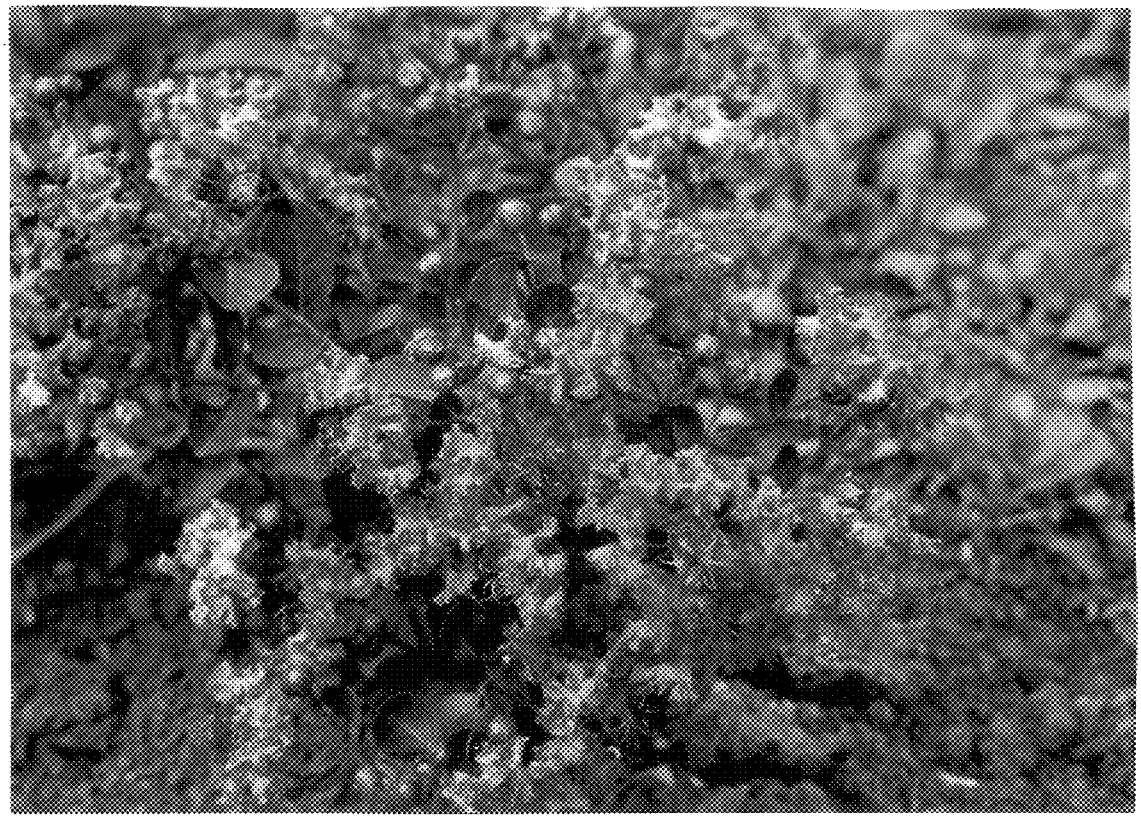

* * * * *